United States Patent [19]

Kilham et al.

[11] Patent Number: 4,910,403
[45] Date of Patent: Mar. 20, 1990

[54] SAMPLING FLOW CELL WITH DIAMOND WINDOW

[75] Inventors: Lawrence B. Kilham, Secaucus; Maurice W. LeBlon, East Brunswick, both of N.J.

[73] Assignee: Flow Vision, Inc., Little Falls, N.J.

[21] Appl. No.: 265,947

[22] Filed: Nov. 2, 1988

[51] Int. Cl.$^4$ ............................................. G01N 21/15
[52] U.S. Cl. ..................................... 250/343; 356/246
[58] Field of Search ........................... 250/343; 356/246

[56] References Cited

U.S. PATENT DOCUMENTS 4,715,711 12/1987 Dunn .................................... 356/246
4,717,827 1/1988 Harvey ................................. 250/343

OTHER PUBLICATIONS

J. M. Alberigs and J. M. L. Penninger, "An Improved Window Seal for High Temperature-Pressure Spectroscopic Flow Cells." *Review of Scientific Instruments*, vol. 45, No. 3 (Mar. 1974) pp. 460-461 [© 1974 by the American Institute of Physics].

L. M. Toth, J. P. Young and G. P. Smith, "Diamond Windowed Cell for Spectrophotometry of Molten Fluoride Salts." *Analytical Chemistry*, vol. 41, No. 4 (Apr. 1969) pp. 683-685.

*Primary Examiner*—Constantine Hannaher
*Attorney, Agent, or Firm*—Samuelson & Jacob

[57] ABSTRACT

A flow cell is utilized on-line in the analysis of molten polymer and includes diamond windows for passing mid to far infrared radiation through the molten polymer flowing through the flow cell, the diamond windows being in the form of relatively thin disk-like elements each affixed to a carrier member in the wall of the flow cell and spanning a relatively large diameter bore in the carrier member, the overall diameter of each disk-like element being only slightly greater than the corresponding bore in the carrier member such that the volume of diamond is minimized in relation to the diameter of the windows.

11 Claims, 2 Drawing Sheets

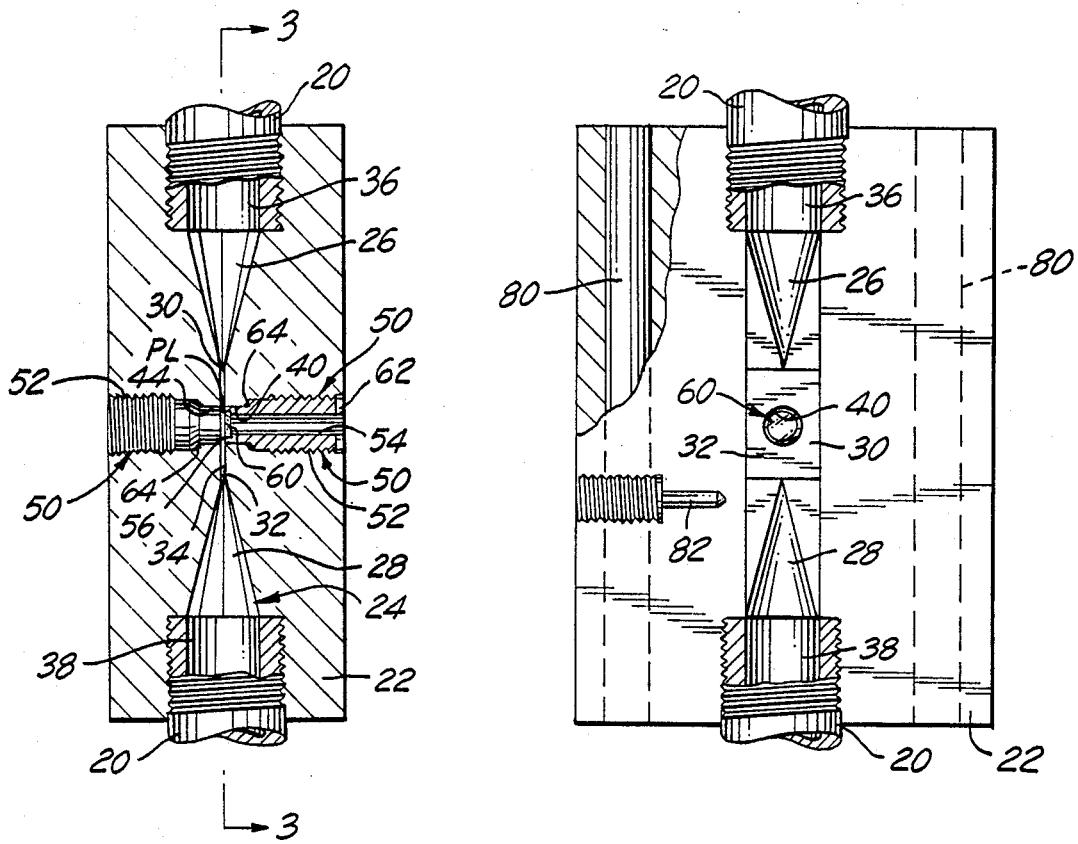
FIG. 2
FIG. 3
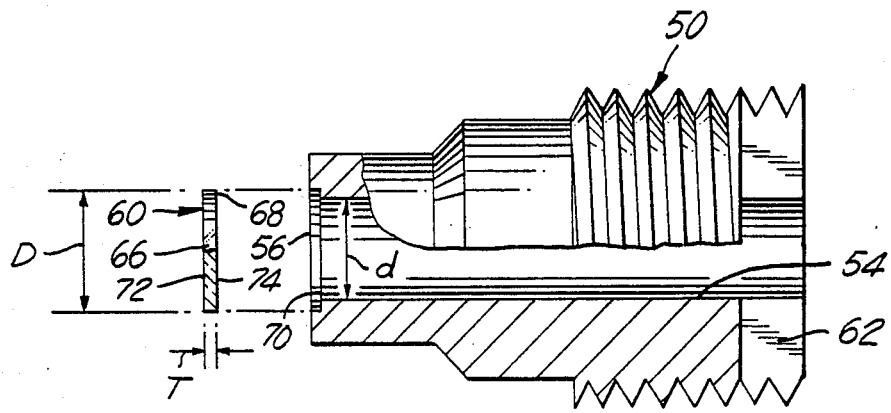
FIG. 4

SAMPLING FLOW CELL WITH DIAMOND WINDOW

The present invention relates generally to continuous sampling flow cells and pertains, more specifically, to optical windows suited for use in connection with the analysis of molten polymers introduced into such flow cells under high pressure and high temperature conditions for analysis with infrared radiation introduced through the optical windows.

Infrared spectroscopy has been in use for some time now and has become a common analytical tool for detecting and measuring the levels of certain chemical constituents appearing in many commercial polymers during manufacture of the polymers. For example, in the manufacture of common commercial polymers, such as polyethylene, infrared spectroscopy has been utilized as an aid in the control of the process through determination of the levels of carbonyl, an oxidation group, the quantity of which is a measure of degradation upstream in the manufacturing process. Another example of the use of infrared spectroscopy techniques is in the measurement of the amounts of vinyl acetate present as a copolymer with polyethylene in the manufacture of adhesives.

Current infrared spectroscopy techniques generally utilize laboratory instruments in which a sample is introduced into the instrument under laboratory conditions. Usually, a sample of the polymer is pressed out to a thickness of about 100 microns, is inserted into the sample cell of the instrument, and a measurement is taken, either at a fixed frequency ("single beam" or "dispersive" infrared) or in a swept range of frequencies to chart the entire spectrum ("Fourier transform infrared" or FTIR). Fixed frequency measurements are carried out at a single wavelength within the range of about 2 to 15 microns, while the frequencies in the swept frequency procedure usually cover the entire range.

These laboratory procedures are effective in providing the desired information; however, because they are laboratory procedures, they have significant limitations in their use in connection with modern high-volume continuous process chemical plants. Laboratory results may not be available for at least an hour after a sample is obtained. During that time, at least 10,000 kg of product may be produced, all of which could be defective, the defects remaining undetected until the laboratory results are known. In a continuous process manufacturing plant, the defective product may even be shipped before the defect becomes known. At a cost of about one dollar per kilogram, it can be appreciated that a system which enables on-line, on-site measurements, and eliminates the need to await laboratory results, can conserve materials and costs. Such a system can be said to operate in real time.

Real-time infrared measurements already are in use in chemical plants. One type of infrared measurement currently in use on-line is known as near infrared (NIR), utilized for measuring levels of constituents in a chemical stream. However, near infrared is limited to the measurement of such constituents as water, in the determination of water content, and can be carried out with relatively inexpensive equipment. In another on-line technique, an instrument measures infrared energy emitted by the flowing chemical itself. In the manufacture of polymers, the wavelength of this passive infrared energy is short, usually less than 2 microns, and the infrared energy is passed through sapphire windows and fiber optic energy guides to the instrument, so as to enable the determination of the temperature of the polymer. The conduct of the infrared energy to and from the chemical stream in both of these techniques is relatively simple and straightforward since known techniques utilizing fiber optic energy guides and sapphire windows are available for use in these measurements. However, these known techniques cannot be used in connection with measurements in the range of frequencies utilized in the present analyses, which frequencies fall into the category known as mid to far infrared (MIR to FIR). Mid and far infrared do not conduct through standard fiber optic bundles and the wavelengths are too long to pass through sapphire windows, since the conduct of infrared through sapphire rolls off at a wavelength of about 5.2 microns.

In addition, in the mid and far infrared spectroscopy in connection with which the present invention is utilized, the windowing and ducting of infrared energy is conducted under high pressure and high temperature conditions in the polymer stream (in the vicinity of at least 7000 psi and 300° C.), presenting problems not encountered in the earlier techniques outlined above. Thus, while sapphire windows are relatively strong and inexpensive, and are suitable for use in connection with near-infrared measurements, these windows do not transmit infrared at wavelengths longer than about 5.2 microns and are not suitable for use in connection with mid and far infrared measurements. Zinc selenide and zinc sulfide have been used in conducting mid to far infrared energy; however, these materials are relatively soft and are susceptible to scratching, erosion, deformation and cracking when subjected to the high pressure and temperature conditions encountered in measurements conducted on molten polymer streams. It is pointed out that molten polymers often are exceptionally abrasive and can cause rapid deterioration of the window material. Regular maintenance or cleaning of such windows cannot counteract the damage caused by contact with the molten polymer stream.

It has been determined that a suitable material for windows used in connection with mid to far infrared measurements in molten polymer streams is diamond. Diamond transmits well at essentially all wavelengths, and especially at wavelengths utilized in connection with infrared spectroscopy, will not corrode, is not affected by abrasion encountered in a molten polymer stream, and can withstand high pressures and temperatures. While diamond windows have been utilized in high pressure sample cells, these windows have been severely limited in diameter and have been too small to be useful in connection with mid to far infrared measurements. A typical example of such a diamond window is found in U.S. Pat. No. 4,715,711, in which there is disclosed a diamond window having a diameter of less than one millimeter. In addition, such diamond windows are quite expensive, primarily due to the amount of diamond utilized. Generally available infrared energy beams require a window diameter of at least several millimeters. Further, the cost of a window in a polymer flow cell should be maintained relatively low, in the vicinity of less than several thousand dollars, in order to find widespread use in the polymer manufacturing industry. In addition, the windows in polymer flow cells should be adjustable to enable selective variation of the distance between opposed windows in a cell since the path length between an entrance window and an exit window is very critical and changes from one polymer to another. The windows should be removed with ease for cleaning and maintenance of the windows and of the flow channels in the flow cell.

Accordingly, the present invention has several objects and advantages, some of which may be summarized as follows: Provides a relatively large-diameter diamond window for flow cells used in connection with mid to far infrared measurements in molten polymers; Enables the practical use of a large-diameter diamond window under the high pressure and high temperature conditions encountered in molten polymer flow cells; Attains on-line measurements utilizing infrared spectroscopy in connection with molten polymers; Provides relatively inexpensive large-diameter diamond windows which are selectively adjustable in flow cells used in connection with infrared measurements in the manufacture of molten polymers; Enables practical instrumentation for on-line measurements in the control of the manufacturing process in the polymer industry.

The above objects and advantages, as well as further objects and advantages, are attained by the present invention, which may be described briefly as an improvement in a material analysis cell of the type in which the material to be analyzed is passed continuously through a chamber in the cell, at high pressures and high temperatures, while being subjected to infrared radiation passed in a given direction through opposed windows in the wall of the cell, the improvement comprising: a tubular carrier member associated with each window, each tubular carrier member including an inner bore having an inner end of prescribed diameter adjacent the chamber and an outer periphery engaging the wall of the cell to retain the windows in the wall of the cell and juxtaposed with the chamber; the windows each being in the form of a diamond having a disk-like configuration including an outer periphery and a very thin wall thickness, in the direction of the infrared radiation, in relation to the overall diameter of the window, the diametric span of the disk-like configuration being only slightly greater than the diameter of the inner bore of the tubular carrier member at the inner end thereof; and each window being affixed adjacent the outer periphery thereof to the tubular carrier member with the diamond spanning the inner bore of the tubular carrier member at the inner end thereof.

The invention will be understood more fully, while still further objects and advantages will become apparent, in the following detailed description of a preferred embodiment of the invention illustrated in the accompanying drawing, in which:

FIG. 2 is an enlarged fragmentary cross-sectional view of the flow cell;

FIG. 3 is a cross-sectional view taken along line 3—3 of FIG. 2; and

FIG. 4 is an exploded longitudinal cross-sectional view of a component of the flow cell.

Figure 1:
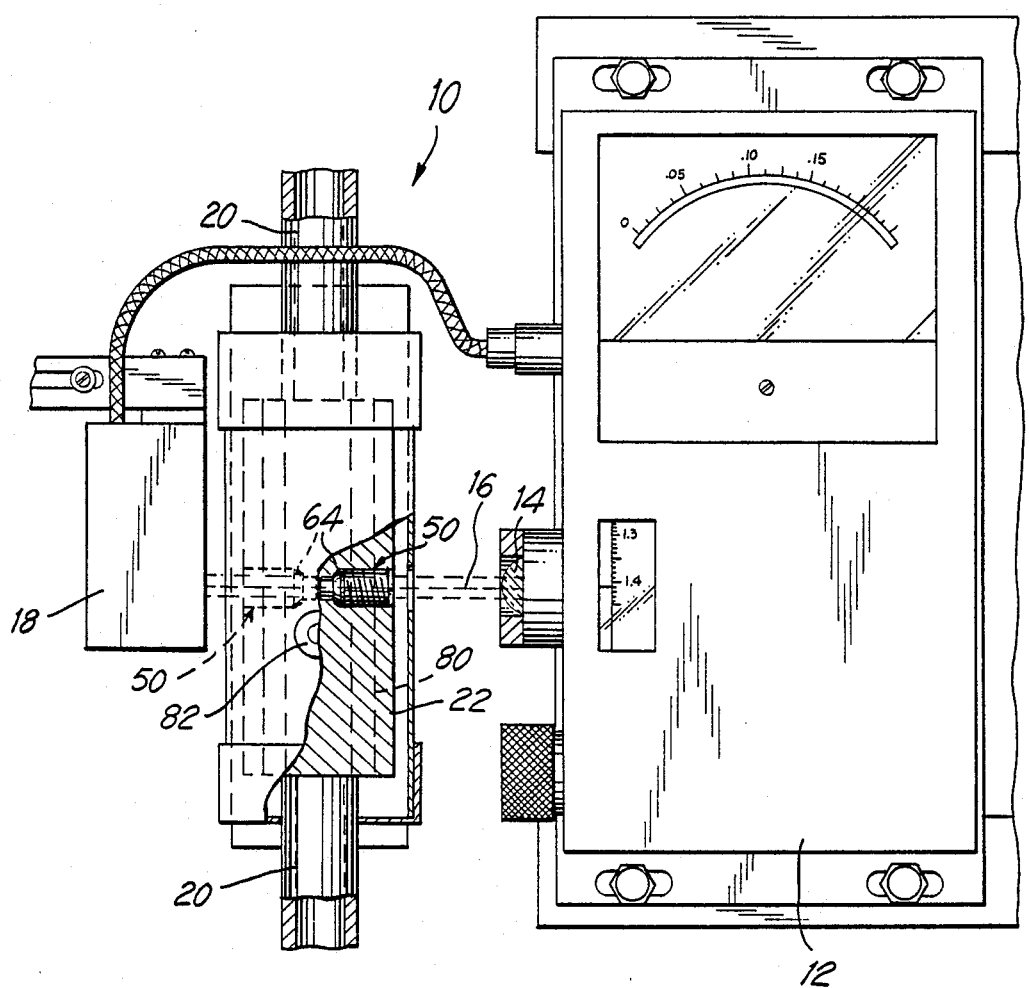
FIG. 1 is a partially diagrammatic elevational view of an apparatus employing the improved flow cell of the present invention.

Referring now to the drawing, and especially to FIG. 1 thereof, an on-line infrared analysis apparatus is shown at 10 and is seen to include a source 12 of infrared energy, the source 12 including an optical system 14 for establishing a collimated beam of infrared radiation directed along a beam path 16 toward a detector 18. A conduit 20 carries the process material to be analyzed, in this instance the material being a molten polymer which flows through conduit 20 under high pressure and high temperature conditions, conduit 20 serving to divert a portion of the full volume of polymer being manufactured in a high-volume continuous production plant. A flow cell 22, constructed in accordance with the present invention, is placed in the conduit 20, in the path 16 of the collimated beam of infrared radiation, so as to enable analysis of the stream of molten polymer in conduit 20 on an on-line basis.

Referring now to FIGS. 2 and 3, as well as to FIG. 1, flow cell 22 includes a flow channel 24 having tapered sections 26 and 28 and a chamber 30 located between the tapered sections 26 and 28. Chamber 30 has a generally rectangular cross-sectional configuration, with a narrow width between opposite walls 32 and 34. The tapered sections 26 and 28 accomplish a smooth transition from the circular cylindrical inlet configuration of channel 24 at 36 to the chamber 30, and from the chamber 30 to the circular cylindrical outlet configuration of channel 24 at 38, respectively. The area of the rectangular cross-sectional configuration of the chamber 30 is approximately equal to the area of the circular cylindrical configuration at the inlet and at the outlet so as to keep the flow rate of the molten polymer essentially constant throughout the length of the travel of the polymer in the channel 24. An input port 40 passes through the wall 32 of flow cell 22 at the chamber 30 and is aligned with the beam path 16 adjacent the source 12. Likewise, an output port 44 passes through the wall 34 of the flow cell 22 at the chamber 30 and is aligned with the beam path 16 opposite the input port 40 and adjacent the detector 18.

A tubular carrier member 50 is located in each port 40 and 44, each carrier member 50 being secured in place by a complementary threaded connection 52 at the outer periphery of the carrier member 50. Each carrier member 50 has a central inner bore 54, the inner end 56 of which is located adjacent the chamber 30. A window 60 is secured at the inner end 56 of each carrier member 50 so as to be placed essentially flush with the wall 42 of the flow cell 22 at the chamber 30. The purpose of the windows 60 is to pass the infrared radiation from the source 12 into the molten polymer in the chamber 30 and thence to the detector 18. The infrared signal received by the detector 18 is converted to electronic data indicative of the properties sought to be measured in the molten polymer. The threaded connections 52 enable selective removal of the carrier members 50 for ease of cleaning, maintenance or replacement of the windows 60 whenever necessary. A wrenching configuration in the form of a slot 62 is provided at the outer end of each carrier member 50 to allow ready rotation of the carrier member 50 in the threaded connection 52. In addition, rotation of the carrier members 50 within the threaded connections enables selective adjustment of the spacing between the windows 60, along the direction of the path 16, and, consequently, the path length PL followed by the infrared radiation through the molten polymer so that the path length PL is optimum for the polymer and the spectroscopic analysis being utilized. For mid tb far infrared spectroscopy, the optimum path length PL typically is in the range of about 100 to 1000 microns. A resilient washer 64 maintains the integrity of the seal between each tubular carrier member 50 and the body of the flow cell 22.

In mid to far infrared spectroscopic analysis, the windows 60 must be capable of passing infrared radiation having wavelengths of about five microns and longer.

The windows 60 must retain that ability despite the high pressure and high temperature conditions to which the windows 60 are exposed, and must resist the abrasion of the molten polymer, as well as erosion, corrosion, deformation, cracking and other modes of failure endemic to the environment in which the windows 60 are utilized. At the same time, it is advantageous to have a window 60 of a diameter great enough to pass sufficient infrared radiation for accurate information despite the presence of contaminants and other inclusions within the molten polymer which tend to lodge in the vicinity of the windows 60 and obstruct the windows 60 during use. Accordingly, windows 60 are constructed of diamond and, as best seen in FIG. 4, each window 60 preferably is in the form of a disk-like element 66 having an outer periphery with a circular contour of a diameter D and a very thin wall thickness T as compared to the diameter D of the element 66. The relatively large diameter D provides sufficient area for the transmission of infrared radiation under the above-outlined conditions, while the relatively thin wall thickness T conserves the volume of diamond so as to keep the cost of the window 60 within practical limits. Thus, in a typical window 60, element 66 has an overall diameter D of about 5.00 mm, while the wall thickness T is about 0.5 mm. The diameter D is only slightly larger than the diameter d of the inner bore 54 of the carrier member 50, which diameter d typically is about 4.25 mm, and element 66 is affixed to the carrier member 50 adjacent the outer periphery of the element 66, along a relatively small peripheral affixation area 68 which lies between the diameters D and d, thereby conserving the volume of diamond. The element 66 is seated within an annular recess 70 in the carrier member 50 to span the inner bore 54 and the preferred method of affixation is by brazing. It has been found that diamond exhibits sufficient strength in tension, so that when element 66 is affixed along the small peripheral affixation area 68, window 60 possesses the requisite strength to withstand the pressures encountered during use. Element 66 has an obverse surface 72 and a reverse surface 74, the obverse and reverse surfaces 72 and 74 preferably being planar and parallel to one another.

As outlined above, the molten polymer flows through the flow cell 22 under relatively high pressures, usually at least as great as 7000 psi, and at high temperatures, in the vicinity of 300° C., on a continuous basis. Electrical heaters 80 are placed within the body of the flow cell 22 and are controlled in response to temperature information supplied by a thermocouple 82 to maintain the walls 32 and 34 of the flow cell 22 at an appropriate temperature for assuring smooth flow of the molten polymer through the flow cell 22. The diamond windows 60 withstand the high temperatures, as well as the high pressures encountered during use. The tubular carrier members 50 are constructed of a material which will withstand the physical and chemical characteristics to which the tubular carrier members 50 are exposed during use, as well as having thermal expansion properties compatible with the diamond of windows 60. One suitable material is molybdenum.

It will be seen that the use of diamond for elements 66 provides windows 60 having highly desirable characteristics, yet does so with relative economy. The diamond elements 66 withstand the high pressures and high temperatures encountered in flow cell 22 without failure. The hardness of the material resists deterioration from abrasion, erosion and the like. The relatively thin wall thickness T of the elements 66 conserve the amount of diamond needed for a window 60, thereby rendering the use of diamond practical. The affixation of each element 66 along only a limited peripheral area 68 enables a relatively large window opening in relation to the overall volume of diamond utilized. Accordingly, the present invention provides a highly effective, practical flow cell for use in on-line measurements in molten polymers, utilizing mid to far infrared techniques.

It is to be understood that the above description of a preferred embodiment of the invention is provided by way of example only. Various details of design and construction may be modified without departing from the true spirit and scope of the invention as set forth in the appended claims.

The embodiments of the invention in which an exclusive property of privilege is claimed are defined as follows:

1. In material analysis cell of the type in which the material to be analyzed is passed continuously through a chamber in the cell, at high pressures and high temperatures, while being subjected to infrared radiation passed in a given direction through opposed windows in the wall of the cell, the improvement comprising:

a tubular carrier member associated with each window, each tubular carrier member including an inner bore having an inner end of prescribed diameter adjacent the chamber and an outer periphery engaging the wall of the cell to retain the windows in the wall of the cell and juxtaposed with the chamber;

the windows each being in the form of a diamond having a disk-like configuration including an outer periphery and a very thin wall thickness, in the direction of the infrared radiation, in relation to the overall diameter of the window, the diametric span of the disk-like configuration being only slightly grater than the diameter of the inner bore of the tubular carrier member at the inner end thereof; and each window being affixed adjacent the outer periphery thereof to the tubular carrier member such that the diamond is essentially integrated with the tubular carrier member with the diamond spanning the inner bore of the tubular carrier member at the inner end thereof.

2. The invention of claim 1 wherein the difference between the diametric span of the disk-like configuration and the diameter of the inner bore of the tubular carrier member at the inner end thereof establishes a minimal affixation area along the outer periphery of the disk-like configuration, and each window is affixed adjacent the outer periphery thereof at the affixation area.

3. The invention of claim 2 wherein the outer periphery of the disk-like configuration has a generally circular contour with a diameter only slightly greater than the diameter of the inner bore of the tubular carrier member at the inner end thereof.

4. The invention of claim 3 wherein the wall thickness of the diamond window is about 0.5 mm.

5. The invention of claim 4 wherein the diamond window includes an obverse surface and a reverse surface, and both the obverse surface and the reverse surface are planar.

6. The invention of claim 5 wherein the obverse surface and the reverse surface are parallel to one another.

7. The invention of claim 4 wherein the diameter of the inner bore of the tubular member is about 4.25 mm, and the diameter of the diamond window is about 5.00 mm.

8. The invention of claim 1 wherein the diamond window includes an obverse surface and a reverse surface, and both the obverse surface and the reverse surface are planar.

9. The invention of claim 8 wherein the obverse surface and the reverse surface are parallel to one another.

10. The invention of claim 1 including mounting means mounting the tubular carrier members for movement relative to one another in directions parallel to the direction of the infrared radiation to enable selective adjustment of the distance between the windows within the chamber of the cell.

11. The invention of claim 10 wherein the mounting means include a threaded connection between each tubular carrier member and the wall of the cell.

* * * * *